United States Patent [19]

Schainholz

[11] 4,342,391
[45] Aug. 3, 1982

[54] INSTRUMENT COUNT MEMORIZER

[76] Inventor: Herbert Schainholz, 316 Locust St., Teaneck, N.J. 07666

[21] Appl. No.: 232,917

[22] Filed: Feb. 9, 1981

[51] Int. Cl.³ .................. B65D 85/62; A61L 3/02; A61L 19/02; B65D 83/10
[52] U.S. Cl. .................... 206/370; 206/459; 211/60 T; 422/310
[58] Field of Search ............ 206/370, 363, 349, 459, 206/438; 422/310; 211/60 T, 60 R

[56] References Cited

U.S. PATENT DOCUMENTS

| | | | |
|---|---|---|---|
| 746,999 | 12/1903 | Schmitz | 206/370 |
| 2,559,636 | 7/1951 | King et al. | 206/370 |
| 3,396,839 | 8/1968 | Shannon et al. | 206/370 |
| 3,564,662 | 2/1971 | Dold | 206/370 |
| 3,696,920 | 10/1972 | Lahay | 206/370 |
| 3,925,014 | 12/1975 | Langdon | 206/370 |
| 4,043,754 | 8/1977 | Sklar | 206/370 |
| 4,046,254 | 9/1977 | Kramer | 206/370 |
| 4,135,868 | 1/1979 | Schainholz | 206/438 |
| 4,229,420 | 10/1980 | Smith et al. | 206/370 |

Primary Examiner—William T. Dixson, Jr.
Attorney, Agent, or Firm—Stewart F. Moore

[57] ABSTRACT

A device for storing sterile instruments and memorizing the count thereof. A main frame includes a plurality of juxtaposed boots, individually and selectively rotatable from open to closed positions. Each open boot stores the handle of an instrument and a rotatable cover plate is locked into position overlaying open and closed boots to apply holding contact pressure against instrument handles inserted in open boots. The number of open boots indicates the number of instruments selected to be stored by the device.

16 Claims, 15 Drawing Figures

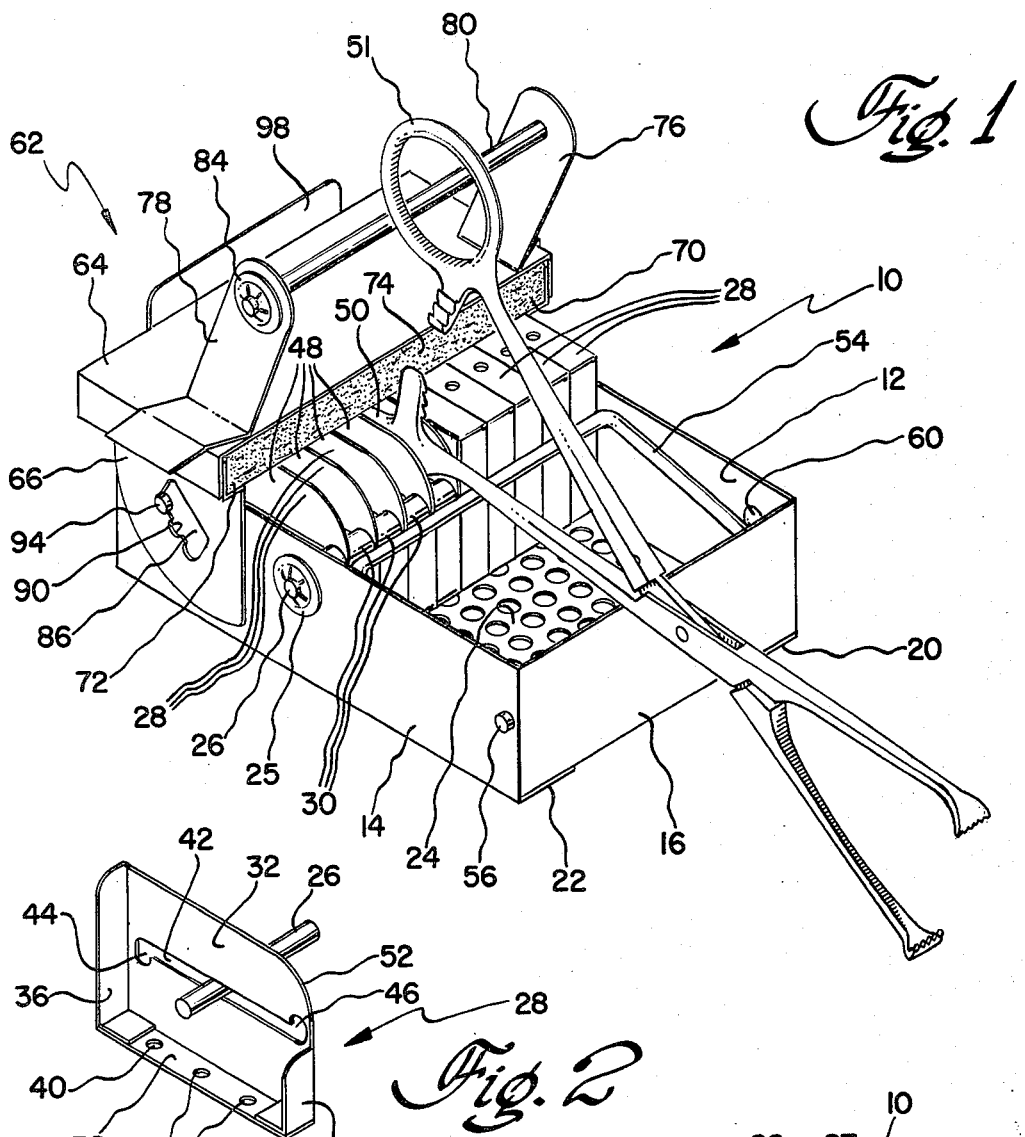

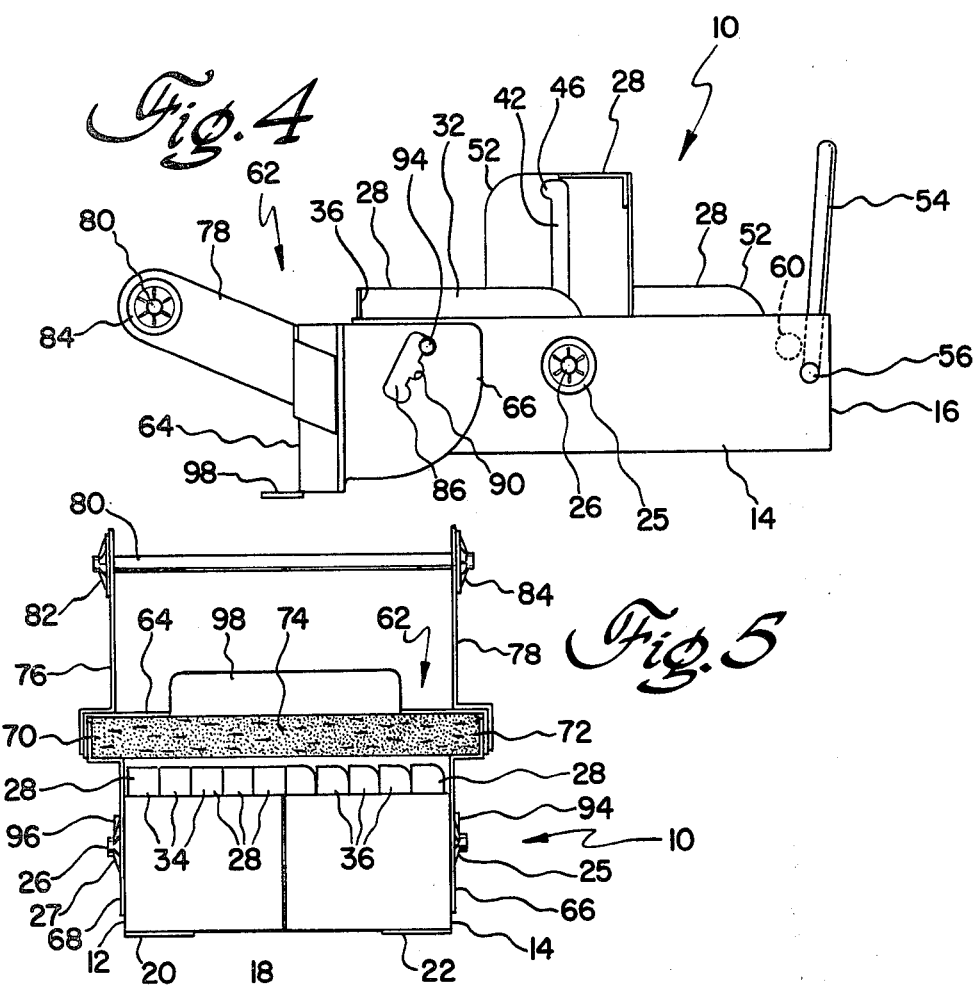
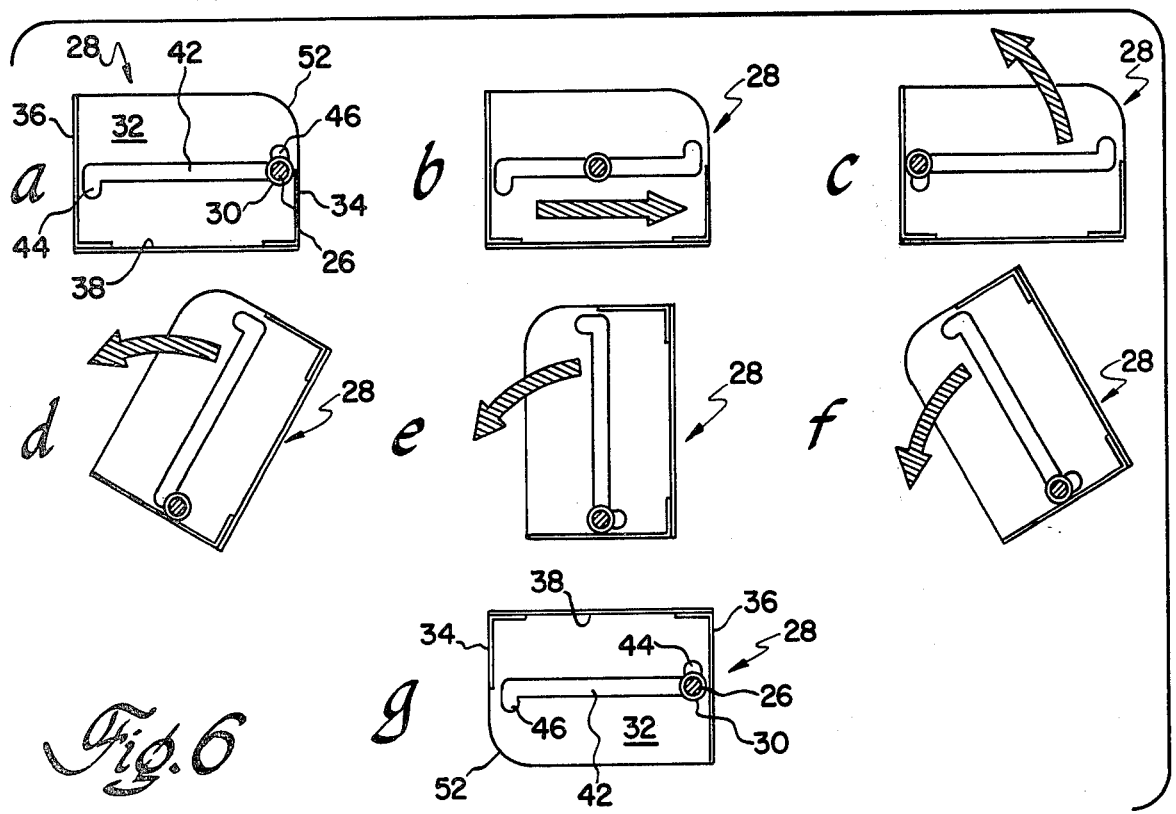

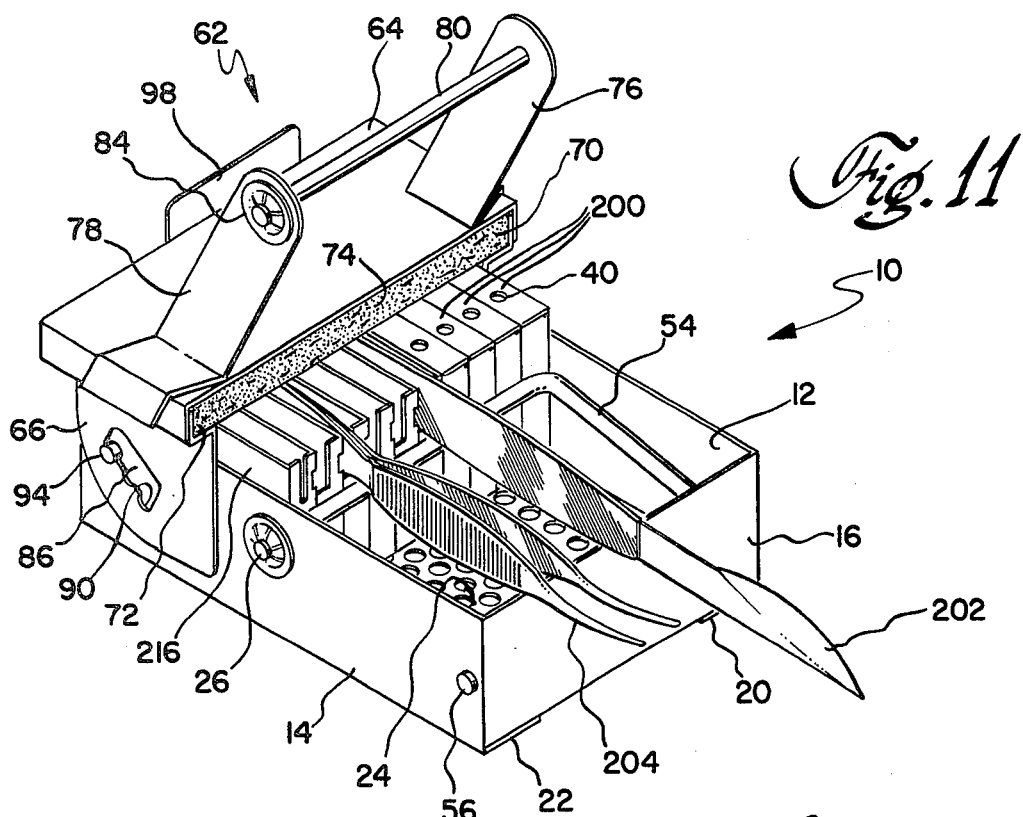
Fig. 11
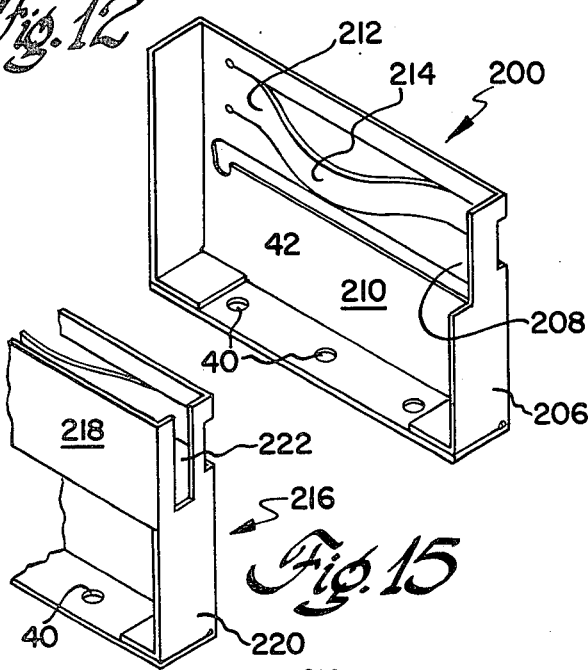
Fig. 12
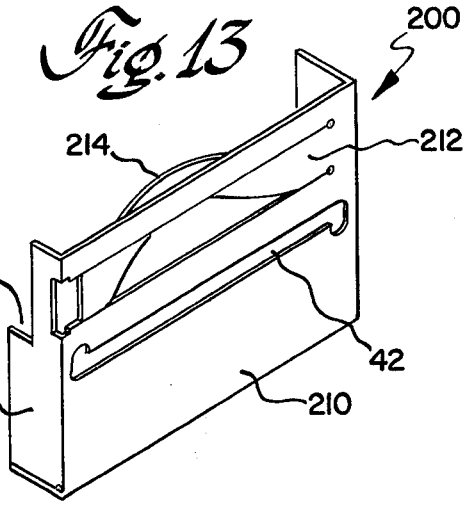
Fig. 13
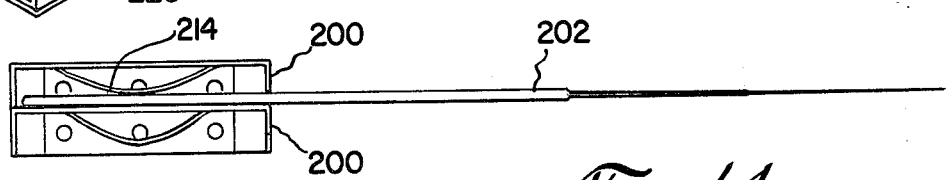
Fig. 15
Fig. 14

INSTRUMENT COUNT MEMORIZER

BACKGROUND OF THE INVENTION

The present invention relates to the handling of tools and particularly surgical instruments, which must be sterilized, counted and carried securely without contact with each other, into an operating room. More specifically, the invention relates to a carrying device for surgical instruments, which retains the instruments in selected positions and memorizes and indicates the total number of surgical instruments carried into an operating room, even though some or all of such instruments are removed from the device during a surgical procedure.

Instruments selected for use in a surgical procedure are usually placed in a sterilization tray in which they are immovably positioned in a manner such that the cutting edges do not come into contact with each other. The tray and instruments are next sterilized together and then presented to operating room personnel for their intended use. It is extremely important that an accurate count be made of the number of instruments so sterilized and presented, and that a count of the number of dirty instruments removed after the surgical procedure is completed be equal to the first count. Otherwise, there is a great risk that one or more instruments unknowingly may have been left inside of a patient after the surgical procedure has been completed, and the surgical incision closed. Although a member of the operating room personnel is usually designated to keep track of the counts, the mental alertness and memory of such person must be relied upon not to make a mistake in counts.

It is therefore an object of the present invention to provide a device for maintaining surgical instruments in an organized arrangement during and after sterilization, while memorizing the count of the number of instruments so maintained.

It is another object of the invention to provide a device for indicating at any time the number of surgical instruments carried by the device into a surgical operating room.

SUMMARY OF THE INVENTION

According to the preferred embodiment of the invention, the above objects are achieved by providing a carrier for surgical instruments which has a plurality of discrete instrument carrying boots arranged in juxtaposed relationship to each other. Each boot is adapted to receive and hold upright one of the rings of a ring handle instrument, or the handle of a flat handle instrument. The discrete boots are arranged on a common positioning bar and are adapted individually to rotate 180 degrees about the bar from an open, instrument handle receiving position to a closed, instrument handle rejecting position. By inserting the handles of selected instruments into corresponding open boots and rotating the unused boots to a closed position the count of the number of instruments selected is mechanically memorized. The count of the instruments initially loaded into the carrier of the invention, whether or not remaining therein at the end of the surgical procedure, is quickly determined by merely counting the total number of open boots. More simply, if the open boots are again filled with dirty instruments after the surgery has been completed, the operating room personnel are assured without having to make an actual count, that the number of instruments that come into an operating room also leave the operating room.

To insure that the memorized count cannot be changed inadvertently as by dropping the entire carrier, a pivotable locking bar is provided which is raised to allow setting of the boots into open and closed positions. The bar is then lowered into abutting relationship with the boots and held in place with a detent, to prevent any further movement of the set boots.

A rotatable cover in accordance with the invention includes a resilient pad which applies a gentle holding pressure against the instrument handles to secure them in their respective boots, when the cover is moved and locked into position overlaying the instrument handles inserted into their respective boots. The movable cover also supports a bar transversely disposed parallel to and overlaying the boots. The bar holds the inserted ring handle instruments in an open condition to facilitate cleaning and sterilization.

The invention is pointed out with particularity in the appended claims. The present invention is best understood by reference to the following detailed description thereof when taken in conjunction with the accompanying drawings in which:

BRIEF DESCRIPTION OF THE DRAWINGS

FIG. 1 is a perspective view of a preferred embodiment of the instrument count memorizing device of the present invention;

FIG. 2 is a perspective view of an instrument retaining boot of the embodiment shown in FIG. 2;

FIG. 3 is a plan view of the embodiment of FIG. 1;

FIG. 4 is a side elevation of the embodiment of FIG. 1, illustrating the cover plate, instrument retaining boots and locking bar in different positions;

FIG. 5 is an end elevation of the embodiment shown in FIG. 1;

FIGS. 6a-g are diagrammatic views illustrating the operation of the instrument retaining boot of FIG. 2;

FIG. 11 is a perspective view of another modification of the embodiment of FIG. 1, illustrating the carrying of flat handle instruments;

FIG. 12 is a perspective view showing one side of an instrument retaining boot of the modification shown in FIG. 11;

FIG. 13 is a perspective view showing another side of the instrument retaining boot shown in FIG. 12;

FIG. 14 is a plan view of a pair of the instrument retaining boots of FIG. 12 with a flat handle instrument inserted in one of the boots;

FIG. 15 is a fragmented perspective view of a modification of the instrument boot shown in FIG. 12.

DESCRIPTION OF THE PREFERRED EMBODIMENTS

Figure 7:
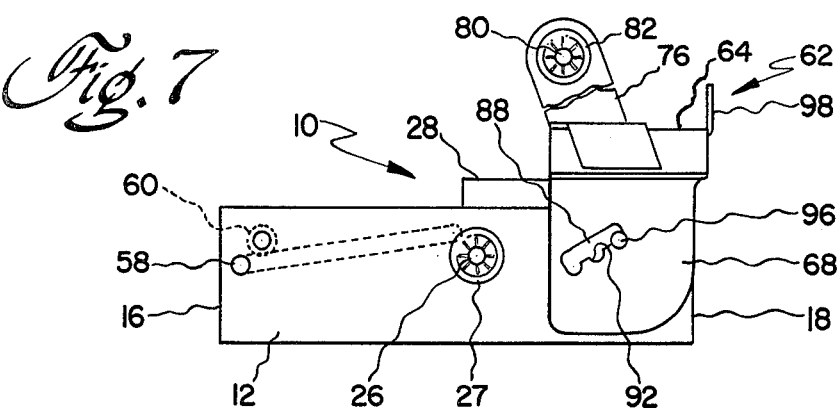
FIG. 7 is a side elevation of the embodiment of FIG. 1.

With reference to FIGS. 1, 3 the instrument count memorizer of the present invention comprises an instrument carrier including a metallic frame 10, preferably made of stainless steel and having a generally rectangular configuration with side members 12, 14 and end members 16, 18. Side members 12, 14 have inwardly extending flaps 20, 22 respectively to provide a support for a floor panel 24, perforated to freely admit and circulate steam for sterilization purposes. Flaps 20, 22 and floor panel 24 are rigidly assembled as by welding, into an open, box-like construction.

A bar 26, transversely positioned between side members 12, 14 and prevented from axial movement by push-on washers 25, 27 has a plurality of discrete, instrument carrying boots 28 mounted thereon in juxtaposed alignment and selectively spaced from each other by means of axially aligned spacing sleeves 30. As shown in more detail in FIG. 2, each boot 28 has a side wall 32, end walls 34, 36 of unequal length, and a floor 38 with perforations 40 to allow sterilizing steam to pass freely therethrough. A second side wall, opposite side wall 32, is not provided since, when in assembled relationship, the side wall 32 of each boot provides suitable side closure for the next adjacent boot. If desired, boot 28 may be integrally formed from a single piece of sheet material, with end walls 34, 36 and floor 38 bent into position and affixed to each other as by welding to form a rigid structure. Intermediate the top and bottom of side wall 32, and extending parallel to floor 38 and laterally for almost the entire length of side walls 32, is an elongated slot 42 which has enlarged ends 44, 46 respectively pointing in opposite directions from each other. Bar 26 passes through each slot 42 which has a width slightly greater than the diameter of the bar to allow boots 28 to slide laterally and rotate freely around bar 26.

With reference to FIGS. 6a–g, it will be seen that each boot 28 is free to slide laterally along floor panel 24 until one of the end enlargements 44, 46 of its associated slot 42 are reached. End enlargements 44, 46 of slot 42 allow boot 28 to be lifted slightly upward when rotation of the boot is desired so that the wall corners of the boot will freely clear floor panel 24 during rotation. In the illustrative example shown in FIG. 6, boot 28 is slid to the right until bar 26 engages enlargement 44 (FIGS. 6a–c). Boot 28 is then rotated 180 degrees about bar 26 in a counterclockwise direction (FIGS. 6d–f), whereupon it returns to its original but now inverted position with end wall 34 disposed closely adjacent to end member 18 of frame 10. Floor 38 now faces upwardly (FIG. 6g), thereby preventing insertion of a ring handle 50 of a hinged surgical instrument. Conversely, when end wall 36 of boot 28 is slidably positioned closely adjacent to end member 18 with enlargement 46 surrounding bar 26 (FIG. 6a), boot 28 cooperates with the side wall 32 of an adjacent boot to form a compartment presenting an opening 48 (FIG. 1) facing upwardly and adapted to receive a ring handle 50 of a surgical instrument.

The length of end wall 34 of boot 28 (FIG. 2) is suitably dimensioned, preferably slightly less than the vertical height of transversely disposed bar 26 above floor panel 24, in order to provide easy insertion of the ring handle 50 into a selected opening 48. Likewise, the corner 52 of sidewall 32 is rounded to facilitate further the insertion of ring handle 50.

The manner in which the instrument count memorizer is used will be apparent from the foregoing. After the number of instruments necessary for a particular surgical procedure has been determined, a like number of boots 28 are arranged by the method just described so that openings 48 face upwardly to receive a corresponding number of instrument ring handles 50. The remaining boots 28 are, of course, inverted with floors 38 facing upwardly to prevent insertion of instrument ring handles therein. It will therefore be seen that the number of openings 48 represents the count of the instruments carried by the present invention through the sterilizing process and into the operating room. Once the selected openings have been filled, the instruments remain stored therein through the sterilizing process and in the operating room until removed for use during the surgical procedure. Since the instrument count has been memorized as represented by openings 48 in boots 28, it will be evident that such openings must be filled with dirty instruments after the surgical procedure has been completed, to insure that all instruments used in the procedure have been retrieved and not left inside the body of a patient.

Referring again to FIGS. 1 and 3, a boot locking bar is provided to prevent further movement of boots 28, after the boots have been arranged into count memorizing positions. Locking bar 54 has a U-shaped configuration with outwardly extending fingers 56, 58 which extend through corresponding apertures in frame side members 12, 14 respectively. A detent button 60, fixedly positioned on frame side member 12 adjacent to the aperture for finger 58, is provided to hold locking bar 54 tightly against boots 28 after they have been arranged to memorize a desired count. When a count is to be memorized, locking bar 54 is pivoted upwardly past detent 60 into a vertical position (FIG. 4) so that boots 28 may be freely slid along floor panel 24 to their extended positions, rotated about bar 26, retracted and reset to form the desired count arrangement. Locking bar 54 is sufficiently resilient to allow fingers 56, 58 to move yieldably towards each other as bar 54 is pushed past detent 60.

After boots 28 have been arranged to reflect a selected instrument count and have been locked into position by downward rotation of locking bar 54, ring handles 50 of selected surgical instruments are each loaded into a corresponding opening 48 of boot 28. A hold down cover 62, pivotally mounted on frame side members 12, 14 is then rotated into locking engagement with ring handles 50.

As shown in FIGS. 1, 3, 4, 5 hold down cover 62, transversely disposed across frame 10 has a laterally extending cover plate 64 with downwardly extending arms 66, 68 attached thereto, which pivotally embrace frame side members 12, 14 respectively. Arms 66, 68 cooperate with cover plate 64 to form channels 70, 72 which receive and hold under compression a rectangular pad 74 formed from a resilient heat resistant material, such as silicone or other rubber-like compound. Also attached to each side of cover plate 64 are outwardly extending support arms 76, 78 which support an instrument handle spreader bar 80 transversely disposed across frame 10. Bar 80 may be attached to arms 76, 78 as by push-on retaining washers 82, 84 or by any other suitable means. As shown in FIGS. 4, 7 each of arms 66, 68 has a slot 86, 88 respectively angularly disposed in a downward direction away from cover plate 64, when the plate is seated adjacent to boots 28. Slots 86, 88 each have a scalloped edge 90, 92 respectively which engage with an associated pivot pin 94, 96 mounted on frame side members 14, 12.

With reference to FIGS. 1, 4, 7, after ring handles 50 have been inserted into selected openings 48 in boots 28, hold down cover 62 is rotated in an upward direction to a position immediately above ring handles 50. It is then pressed downwardly to cause pad 74 to deform and apply a firm holding pressure against the ring handles 50 nestled in openings 48. Hold down cover 62 will then be locked in position, securely holding ring handles 50 in place because of the upward pressure exerted against the cover by deformed pad 74, which causes a selected scallop of slot edges 90, 92 in arms 66, 68 to press against pivot pins 94, 96. An outwardly extending tab 98, integrally formed on cover plate 64 is provided to facilitate the manipulation of hold down cover 62. A plurality of scallops in edges 90, 92 are provided to allow adjustment of the pressure applied by pad 74, thus accomodating instruments with ring handles of different sizes. Support arms 76, 78 are angularly disposed with respect to cover plate 64 and lean forwardly towards frame end member 16 when hold down cover is in a locking position, thereby holding ring handles 51, which are arranged to rest on bar 80, in an open position to facilitate sterilization of the counted instruments.

Figure 8:
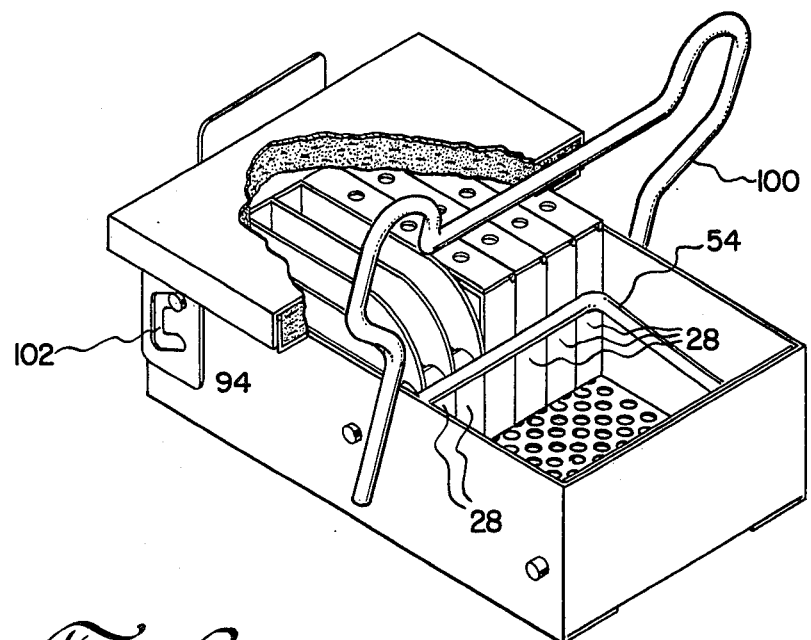
FIG. 8 is a perspective view of a modification of the present invention.
Figure 9:
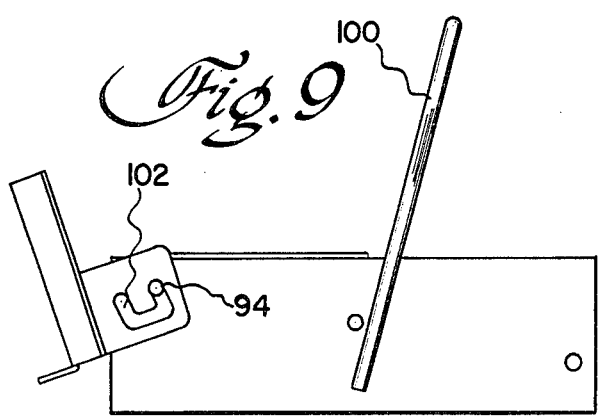
FIG. 9 is a view of the embodiment of FIG. 8, showing the operation of the cover plate.

A modification of the invention is shown in FIGS. 8, 9, wherein a ring handle spreader bar 100 and associated support arms, formed from a continuous length of rod stock material, are attached as by welding to a selected position on frame side members 12, 14, preferably adjacent to bar 26. Bar 100 is angularly disposed with respect to cover plate 64 in a manner similar to bar 80, to provide a selected amount of opening between ring handles 50, 51. In accordance with this modification of the invention, a convenient handle for transporting the count memorizer is provided by bar 100.

Figure 10:
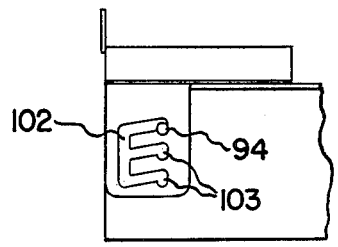
FIG. 10 is a fragmented side view of a modification of the embodiment of FIG. 8.

The locking arrangement provided by slots 86, 88 and pivot pins 94, 96 may also be modified to provide a more secure lock for hold down cover 62. As shown in FIGS. 8, 9, slots 86, 88 may be formed into a modified bayonet configuration 102 to provide stepped positions so that cover plate 62 may exert different amounts of pressure on instrument handles inserted in open boots 28. To further insure that cover plate 62 will not unlock during periods of rough handling of the count memorizer, the ends of slots 102 may be provided with enlargements 103 as shown in FIG. 10. Pivot pin 94, pressing against a selected enlargement 103 locks cover plate 62 in position in such a manner that it cannot be released until resilient pad 74 is further compressed by pressing cover plate 62 towards boots 28.

FIG. 11 illustrates a modification of the present invention to provide memorization of the count of other than ring handle instruments, such as thumb forceps, scalpels, leaf handle instruments or other flat handle instruments. In particular, instrument carrying boots 200 are provided which are similar to boots 28 but modified to receive the flat handles of instruments such as knife 202 and thumb forceps 204.

As shown in more detail in FIGS. 12, 13, 14 boot 200 has an upwardly extending end wall 206 and a notched out portion forming a slot-like configuration 208, which allows a flat handle instrument to be inserted into boot 200 and rest in a substantially horizontal position. Boot 200 has a side wall 210 in which a resilient finger 212 is formed as by lancing. Finger 212 has an inwardly protruding deformation 214 which, when boots 200 are assembled in a juxtaposed relationship as seen in FIG. 14, applies pressure against the flat side of the handle of an instrument such as knife 202, or thumb forceps 204. The flat handle is thereby urged against the wall 210 of the next adjacent boot 200, to hold it securely nestled in its associated boot 200.

Boot 216, disposed adjacent side frame member 14 has a side plate 218 (FIG. 15) laterally extending between end walls 36 and 220, and affixed thereto to provide an additional support wall when a flat handle instrument is inserted therein. Plate 218 prevents an instrument inserted into boot 216 from dislocating or falling out of the boot. A slot 222, formed in end plate 220 aids in properly positioning the handle on an instrument inserted in boot 216. The operation of the embodiment of FIG. 11 to store flat handle instruments and memorize an instrument count is the same as described for the embodiment of FIGS. 1-6.

While this invention has been shown and described in the best forms known, it will nevertheless be understood that this is purely exemplary and that modifications may be made without departing from the spirit of the invention.

I claim:

1. A count memorizing device for instruments of the type having at least one handle for manual manipulation thereof comprising, a carrier for storing a plurality of said instruments, a plurality of boots disposed in said carrier and individually movable from open to closed positions, each of said boots when in said open position having means for receiving the handle of a discrete instrument to hold said instrument in an outwardly extending position, and locking means operative to maintain said boots in selected open and closed positions, the number of open boots indicating the number of instruments selected to be stored by said carrier.

2. The invention defined in claim 1, wherein said locking means includes a rotatable cover plate, and means supported by said carrier for rotatably mounting said cover plate in a position effective to apply holding contact pressure against said boots and said instrument handles inserted in said boots.

3. The invention defined in claim 2, including a block of resilient material, and wherein said cover plate includes means holding said block of resilient material in a position operative to apply holding contact pressure against said boots and said instrument handles.

4. The invention defined in claim 2, including adjustable means cooperating with said carrier for adjustably locking said cover plate in said selected position.

5. The invention defined in claim 4 wherein said adjustable means includes a pair of pivot pins outwardly extending from said carrier and a pair of depending arms extending from said cover plate, each of said arms having a slot with a configuration defining a plurality of stepped positions, each of said slots cooperating with a corresponding one of said pivot pins to adjustably lock said cover plate at a selected one of said stepped positions.

6. The invention defined in claim 2, including a bar vertically spaced from said boots and transversely disposed thereto when said cover is in said contact pressure applying position, and supporting arms outwardly extending from said cover plate to support said bar, said bar being operative to displace vertically one handle of an elongated hinged instrument having another handle resting in one of said boots.

7. The invention defined in claim 1 wherein said boots are arranged in said carrier in juxtaposition with each other.

8. The invention defined in claim 7 wherein each boot has at least a floor and a side wall, said side wall cooperating with the side wall of an adjacent juxtaposed boot to form a compartment with an opening for receiving an instrument handle when said boot is in said open position, said floor being operative to prevent insertion of an instrument handle in said boot when said boot is inverted from said open position to said closed position.

9. The invention defined in claim 8 wherein each boot further has at least one end wall, said end wall having a slot for receiving the handle of a flat handle instrument when said boot is in said open position, said side wall having a resilient finger inwardly extending to abut said flat handle and urge said handle against the side wall of an adjacent boot to hold securely said handle in said boot.

10. The invention defined in claim 7, including aligning means connected to said carrier for maintaining said boots in juxtaposed alignment.

11. The invention defined in claim 10 wherein said aligning means comprises a bar supported by said carrier, and each of said boots is rotatably mounted on said bar.

12. The invention defined in claim 7 wherein each of said boots has an upstanding end wall and wherein said locking means further includes removable means for abuttingly engaging said end walls of said boots to hold said boots in selected open and closed positions.

13. The invention defined in claim 12 wherein said removable means includes a U-shaped bar having upstanding arms pivotally attached to said carrier, said U-shaped bar being operative to rotate into engagement with said end walls, and detent means for removably holding the base of said U-shaped bar in engagement with said end walls.

14. The invention defined in claim 7, including spreader means associated with said carrier vertically spaced from said boots and transversely disposed thereto, and operative to displace vertically one handle of an elongated hinged instrument having another handle stored in one of said boots.

15. A count memorizing device for instruments of the type having at least one handle for manual manipulation thereof comprising, a frame for supporting a plurality of said instruments, said frame having a bottom member and side members forming a box-like configuration, a plurality of boots disposed within said frame and arranged in juxtaposition with each other, each of said boots being individually movable from open to closed positions and having at least a floor and a side wall, said side wall cooperating with the side wall of an adjacent boot to form a compartment with an opening for receiving an instrument handle when said boot is in said open position, said floor being operative to prevent insertion of an instrument in said boot when said boot is inverted from said open position to said closed position, each side wall of said boots having an elongated slot therein disposed intermediate the top and bottom thereof and parallel to the floor of an associated boot, aligning means for maintaining said boots in juxtaposed alignment including a bar extending between said side members of said frames and passing through said slots to rotatably mount said boots on said bar, each of said boots being operative to be rotatably inverted about said bar from an open position with the floor of said boot abutting the bottom member of said frame, to a closed position with the top of said side wall abutting the bottom member of said frame, and locking means to maintain said boots in selected open and closed positions, the number of open boots indicating the number of instruments selected to be transported by said carrier.

16. The invention defined in claim 15 wherein each end of said slot in said sidewall terminates in an enlarged area operative to allow said associated boot to rotate freely about said bar in said enlarged areas.

* * * * *